United States Patent
Dragoi et al.

(10) Patent No.: US 7,829,862 B2
(45) Date of Patent: Nov. 9, 2010

(54) RADIATION SENSOR DEVICE AND FLUID TREATMENT SYSTEM CONTAINING SAME

(75) Inventors: Catalina Dragoi, Madison, AL (US); Alex Verdun, London (CA); Jim Fraser, St. Thomas (CA); Jennifer Gerardi, St. Thomas (CA); Tanya Molyneux, St. Thomas (CA)

(73) Assignee: Trojan Technologies Inc. (CA)

( * ) Notice: Subject to any disclaimer, the term of this patent is extended or adjusted under 35 U.S.C. 154(b) by 0 days.

(21) Appl. No.: 11/166,348

(22) Filed: Jun. 27, 2005

(65) Prior Publication Data

US 2006/0006332 A1 Jan. 12, 2006

Related U.S. Application Data

(60) Provisional application No. 60/583,614, filed on Jun. 30, 2004.

(51) Int. Cl.
*G01J 3/02* (2006.01)
*A62D 3/176* (2007.01)
(52) U.S. Cl. .................. 250/372; 250/373; 588/309
(58) Field of Classification Search .............. 250/372, 250/373; 257/E21.054, E31.093; 588/309
See application file for complete search history.

(56) References Cited

U.S. PATENT DOCUMENTS

| | | | |
|---|---|---|---|
| 4,880,533 A * | 11/1989 | Hondulas | 210/104 |
| 5,159,455 A | 10/1992 | Cox et al. | |
| 5,327,770 A | 7/1994 | Hindle | |
| 5,448,362 A | 9/1995 | Perchak | |
| 5,504,335 A | 4/1996 | Maarschalkerweerd | |
| 6,080,313 A * | 6/2000 | Kelada | 210/631 |
| 6,429,438 B1 * | 8/2002 | Smestad | 250/373 |
| 6,459,087 B1 * | 10/2002 | Kaas | 250/372 |
| 6,512,234 B1 * | 1/2003 | Sasges et al. | 250/373 |
| 6,612,120 B2 | 9/2003 | Patel et al. | |
| 6,655,223 B2 * | 12/2003 | March et al. | 73/866.5 |
| 6,791,092 B2 * | 9/2004 | Hamilton | 250/373 |
| 7,049,602 B2 * | 5/2006 | Tokhtuev et al. | 250/372 |
| 2001/0046461 A1 | 11/2001 | Hamilton | |

OTHER PUBLICATIONS

Office Action for Canadian Patent Application No. CA 2,571,129 with a mailing date of Jan. 27, 2009.
First Office Action for Chinese Patent Application No. 200580022354.5, mailing date of Jul. 2009.

* cited by examiner

*Primary Examiner*—David P Porta
*Assistant Examiner*—Casey Bryant
(74) *Attorney, Agent, or Firm*—Katten Muchin Rosenman LLP

(57) ABSTRACT

The invention relates to a radiation sensor device comprising a housing and a plurality of radiation sensor modules secured to the housing. Each radiation sensor module comprises a radiation sensor arranged to detect radiation incident on the radiation source module. Preferably, each radiation sensor module contains an entire so-called optical train to allow for calibration of the detector (e.g., photodiodes, photoresistors and the like) without disassembling all the components of the module.

25 Claims, 3 Drawing Sheets

RADIATION SENSOR DEVICE AND FLUID TREATMENT SYSTEM CONTAINING SAME

CROSS-REFERENCE TO RELATED APPLICATION

The present application claims the benefit under 35 U.S.C. §119(e) of provisional patent application Ser. No. 60/583,614, filed Jun. 30, 2004, the contents of which are hereby incorporated by reference.

BACKGROUND OF THE INVENTION

1. Field of the Invention

In one of its aspects, the present invention relates to a radiation sensor device. In another of its aspects, the present invention relates to a fluid treatment system comprising a novel radiation sensor device. In yet another of its aspects, the present invention relates to a radiation sensor module for use in a radiation sensor device.

2. Description of the Prior Art

Optical radiation sensors are known and find widespread use in a number of applications. One of the principal applications of optical radiation sensors is in the field of ultraviolet radiation fluid disinfection systems.

It is known that the irradiation of water with ultraviolet light will disinfect the water by inactivation of microorganisms in the water, provided the irradiance and exposure duration are above a minimum "dose" level (often measured in units of microwatt seconds per square centimeter). Ultraviolet water disinfection units such as those commercially available from Trojan Technologies Inc. under the tradenames Trojan UV Max™, Trojan UV Logic™ and Trojan UV Swift™, employ this principle to disinfect water for human consumption. Generally, water to be disinfected passes through a pressurized stainless steel cylinder which is flooded with ultraviolet radiation. Large scale municipal waste water treatment equipment such as that commercially available from Trojan Technologies Inc. under the trade-names UV3000™, UV3000 Plus™ and UV4000™, employ the same principal to disinfect waste water. Generally, the practical applications of these treatment systems relates to submersion of treatment module or system in an open channel wherein the wastewater is exposed to radiation as it flows past the lamps. For further discussion of fluid disinfection systems employing ultraviolet radiation, see any one of the following:

U.S. Pat. No. 4,482,809,
U.S. Pat. No. 4,872,980,
U.S. Pat. No. 5,006,244,
U.S. Pat. No. 5,418,370,
U.S. Pat. No. 5,539,210, and
U.S. Pat. No. Re 36,896.

In recent years, such systems have also been successfully used for other treatment of water—e.g., taste and odour control, TOC (total organic carbon) control and/or ECT (environmental contaminant treatment).

In many applications, it is desirable to monitor the level of ultraviolet radiation present within the water under treatment. In this way, it is possible to assess, on a continuous or semi-continuous basis, the level of ultraviolet radiation, and thus the overall effectiveness and efficiency of the disinfection process.

It is known in the art to monitor the ultraviolet radiation level by deploying one or more passive sensor devices near the operating lamps in specific locations and orientations which are remote from the operating lamps. These passive sensor devices may be photodiodes, photoresistors or other devices that respond to the impingent of the particular radiation wavelength or range of radiation wavelengths of interest by producing a repeatable signal level (in volts or amperes) on output leads.

Conventional ultraviolet disinfection systems often incorporate arrays of lamps immersed in a fluid to be treated. Such an arrangement poses difficulties for mounting sensors to monitor lamp output. The surrounding structure is usually a pressurized vessel or other construction not well suited for insertion of instrumentation. Simply attaching an ultraviolet radiation sensor to the lamp module can impede flow of fluid and act as attachment point for fouling and/or blockage of the ultraviolet radiation use to treat the water. Additionally, for many practical applications, it is necessary to incorporate a special cleaning system for removal of fouling materials from the sensor to avoid conveyance of misleading information about lamp performance.

International Publication Number WO 01/17906 [Pearcey] teaches a radiation source module wherein at least one radiation source and an optical radiation sensor are disposed within a protective sleeve of the module. This arrangement facilitates cleaning of the sensor since it is conventional to use cleaning systems for the purposes of removing fouling materials from the protective sleeve to allow for optimum dosing of radiation—i.e., a separate cleaning system for the sensor is not required. Further, since the optical radiation sensor is disposed within an existing element (the protective sleeve) of the radiation source module, incorporation of the sensor in the module does not result in any additional hydraulic head loss and/or does not create a "catch" for fouling materials.

Conventional radiation sensor devices typically have been designed as field units with the detector (e.g., photodiodes, photoresistors and the like) being calibrated prior to assembly into the sensor body. The sensor body is then sealed in a conventional manner to prevent ingress of fluid.

Recently, the United States Environmental Protection Agency ("USEPA") published guidelines for ultraviolet radiation sensor devices for use in municipal drinking water treatment systems. These published guidelines prescribe the use of one sensor per radiation source in municipal drinking water treatment water systems. The published guidelines also prescribe: the use of one or more filters to limit the sensitivity of the detector (e.g., photodiodes, photoresistors and the like) to the germicidal range, limitations on accuracy/tracability of the sensor device, requirements for regular sensor recalibration and a requirement that UV intensity sensors should view a point along the length of the lamp that is between the electrodes (lamp end) and within 25% of the arc length away from the electrode.

The incorporation of a filter into a sensor device can create a degree of uncertainty if it is not possible to calibrate the specific detector (e.g., photodiodes, photoresistors and the like) paired with the specific filter. If the specific detector is calibrated alone before being paired with the specific filter in the final application, small variations in the composition of the filter and/or position of the filter could impact the sensitivity of the detector and reduce the accuracy of the sensor when compared to an absolute irradiance or radiation dose.

In conventional ultraviolet radiation sensor devices, it is not possible to physically adjust the calibration set point of the detector without first completely dissembling the sensor device.

Accordingly, there remains a need in the art for a sensor device ideally suited to match a specific sensor to a specific radiation source in a 1:1 ratio and to allow for ready removal of the sensor device, verification of calibration of the detector (e.g., photodiodes, photoresistor and the like) and adjustment thereof as required.

SUMMARY OF THE INVENTION

It is an object of the present invention to obviate or mitigate at least one of the above-mentioned disadvantages of the prior art.

It is an object of the present invention to provide a novel radiation sensor device which obviates or mitigates at least one of the above-mentioned disadvantages of the prior art.

It is another object of the present invention to provide a novel radiation sensor module which obviates or mitigates at least one of the above-mentioned disadvantages of the prior art.

Accordingly, in one of its aspects, the present invention provides a radiation sensor device comprising a housing and a plurality of radiation sensor modules secured to the housing, each radiation sensor module comprising a radiation sensor arranged to detect radiation incident on the radiation sensor.

In another of its aspects, the present invention provides a fluid treatment system comprising a fluid treatment zone having disposed therein a plurality of radiation sources and the radiation sensor device a radiation sensor device comprising a housing and a plurality of radiation sensor modules secured to the housing, each radiation sensor module comprising a radiation sensor arranged to detect radiation incident on the radiation source module.

In yet another of its aspects, the present invention provides radiation sensor module comprising a module housing, a radiation sensor secured to the module, a radiation transparent window through which incident radiation may pass to contact the radiation sensor and a calibration element for calibration of a signal received from the radiation sensor.

Thus, the present inventors have discovered a novel radiation sensor device comprising a housing and a plurality of radiation sensor modules secured to the housing. The radiation sensor source modules are, in effect, repeating units that are preferably arranged annularly with respect to the housing so that the ratio of radiation sensor modules to radiation sources is 1:1.

The plurality of radiation sensor modules are positioned on the housing in such a manner as to be able to view a length of lamp that is within 25% of the arc length as measured form a lamp end or electrode.

By using the configuration of sensors as described herein, it is possible to position at least 2 or more sensors on a single support and be positioned to view a lamp within the region 25% of the arc length away from the electrode.

Preferably, each radiation sensor module contains an entire so-called optical train (e.g., one or more of photodiodes, photoresistors, filters, apertures, calibration elements, signal amplification elements, signal transmitter elements and the like) to allow for calibration of the detector without disassembling all the components of the module.

Thus, a given radiation sensor module may be readily removed from the radiation sensor device and calibration of the detector or radiation sensor (e.g., photodiodes, photoresistor and alike) can be readily verified and adjusted, if necessary, all without the need to disassemble the device.

The present radiation sensor device may be readily retrofitted into existing ultraviolet radiation water treatment systems such that these systems are in compliance with the guidelines recently published by the USEPA.

In a first preferred embodiment of the present invention, the optical radiation sensor comprises a radiation detector and a body portion. The radiation detector contains a photodiode or other sensing element which is able to detect and respond to incident radiation. The body portion houses one or more of electronic components, mirrors, optical components and the like. The optical radiation sensor is disposed within a protective sleeve. The protective sleeve may comprise first radiation transparent region in substantial alignment with the radiation detector (or sensing element) and a radiation opaque second region which is in substantial alignment with the body portion of the sensor. Those of skill in the art will also appreciate that the sensing element may be protect by its own integral protective (e.g., quartz) sleeve which may be positioned inside a lamp sleeve, the latter being coated to provide thermal protection.

Throughout this specification, reference is made to a preferred embodiment of the present invention with a protective sleeve containing a "radiation transparent" region and a "radiation opaque" region. Of course, those of skill in the art will recognize that these terms will depend on the nature of radiation present in the radiation field. For example, if the present invention is employed in an ultraviolet (UV) radiation field, it is principally radiation in this portion of the electromagnetic spectrum to which the "radiation opaque" region should be opaque—i.e., the radiation opaque region may be transparent to radiation having characteristics (e.g., wavelength) different than radiation to be blocked. By "radiation opaque" is meant that no more than 5%, preferably no more than 4%, preferably no more than 3%, of the radiation of interest (e.g., this could be radiation at all wavelengths or at selected wavelengths) from the radiation field will pass through the region and impinge on the radiation sensing element. Thus, in some embodiments of the invention, all radiation (e.g., one or more of UV, visible and infrared radiation) present in the radiation field will be blocked to achieve thermal protection of the sensor in addition to eliminating impingement of incident radiation. In other embodiments of the invention, a pre-determined portion of radiation (e.g., one or two of UV, visible and infrared radiation) present in the radiation field will be blocked to achieve thermal protection of the sensor while allowing impingement of a pre-determined portion of incident radiation.

Depending on the radiation field in question, the radiation opaque region may be provided on the protective sleeve in a number of different ways. For example, it is possible to utilize a metallic layer disposed on the interior or exterior of the protective sleeve to confer radiation opacity to the protective sleeve. The metallic layer may compromise at least one member selected from the group comprising stainless steel, titanium, aluminum, gold, silver, platinum, nitinol and mixtures thereof. Alternatively, a ceramic layer may be disposed on the interior or the exterior of the protective sleeve to confer radiation opacity to the protective sleeve. In yet another embodiment, the radiation opaque layer may comprise of porous metal structure and combination with a metal material. The porous metal structure may contain a metal selected from the group of metallic layers referred to above. Examples of non-metal materials in this embodiment of the radiation opaque layer include an elastomer or other material (e.g., PTFE Teflon) secured to the porous metal structure.

In another embodiment, radiation specific opacity may be conferred to the protective sleeve by placement in the interior or the exterior thereof a filter layer which will exclude deleterious radiation but allow radiation of interest to pass through the protective sleeve to be detected by the sensor. Thus, again using the example of an ultraviolet radiation sensor, in many cases, the wavelength of interest for detection is in the range of from about 210 to about 300 nm. It is possible to utilize a layer made from a filter material which will allow substantially only radiation in this range through the protective sleeve allowing detection of radiation while minimizing or preventing thermal build-up compared to the situation where all radiation from the radiation field is allowed to enter the protective sleeve. Non-limiting examples of suitable such filter materials may be made from heavy metal oxides of varying thickness and/or numbers of layers depending on the type of radiation being sensed. Those of skill in the art will further appreciate that the optical radiation sensor may have a thermal opaque region as well as a filtered region to protect the sensing element (e.g., photodiode) of the optical radiation sensor.

The provision of the radiation transparent region may take a number of forms. This can be achieved by physically placing a metal layer or depositing a metal layer on the interior or exterior of the protective sleeve such that the radiation transparent region has a desired shape. For example, the radiation transparent region may have an annular shape, a non-annular shape, a rectilinear shape, a curvilinear shape, a substantially circular shape and the like. Further, the radiation opaque region may be designed to provide a plurality (i.e., two or more) of radiation transparent regions.

The manner of disposing the radiation opaque region on the protective sleeve is not particularly restricted. For example, the radiation opaque layer may be adhered, mechanically secured or friction fit to the protective sleeve. The latter two approaches work particularly well when the radiation opaque layer is disposed on the exterior of the protective sleeve. For the interior of the protective quartz sleeve, it is possible to insert a split expanding sleeve. The first approach is preferred in the case where the radiation opaque layer is disposed on the interior or exterior of the protective sleeve. This approach may be used to deposit a fully or selective radiation opaque layer, for example, via vapor deposition, electron beam gun deposition or the like of a metal oxide (e.g., silicon dioxide, titanium dioxide, etc.).

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

Figure 1:
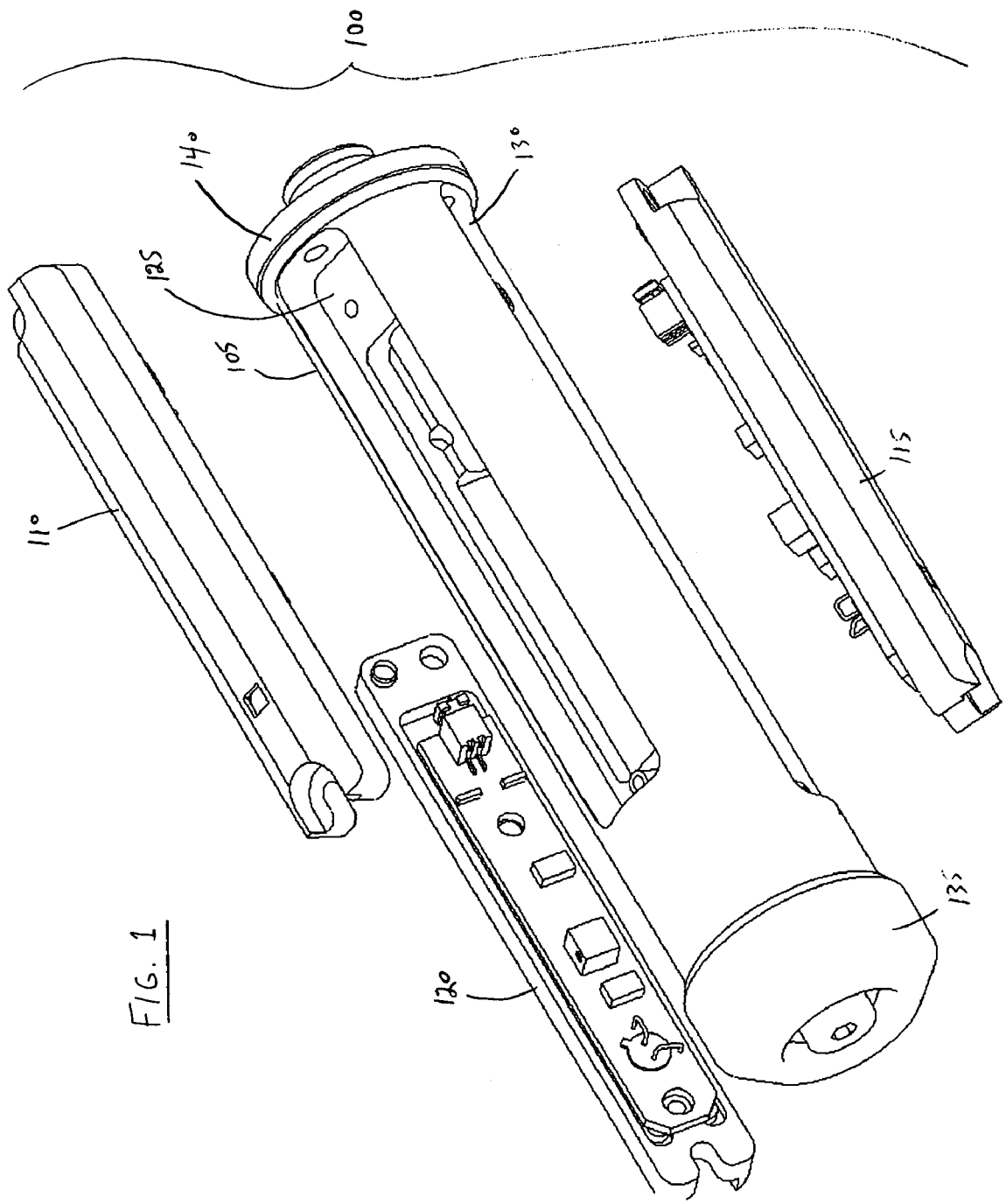
FIG. 1 illustrates a perspective view of a preferred embodiment of the present radiation sensor device having the radiation sensor modules removed therefrom for illustrative purposes.

With reference to FIG. 1 there is illustrated a radiation sensor device 100 comprising a housing 105 and a trio of radiation sensor modules 110, 115, 120. As will be discussed with reference to FIGS. 2 and 3, radiation sensor modules 110, 115, 120 are of identical construction.

Disposed in housing 105 is a cavity 125 to receive each of radiation sensor modules 110, 115, 120 (i.e., one cavity 125 is provided for each radiation sensor module). As shown, cavity 125 and an adjacent cavity are staggered with respect to one another along a longitudinal axis of housing 105 resulting in staggered placement of radiation sensor modules along this axis. This allows for miniaturization of housing 105 on one hand while providing for adequate space for electrical connections to be made to each of radiation sensor modules 110, 115, 120. This also allows for the radiation sensors modules 110, 115, 120 to have their respective aperture windows 152 located toward one end of the housing 105.

Once each of radiation sensor modules 110, 115, 120 are seated in their respective cavities, a protective sleeve (not shown) may be placed over housing 105 between a first end 135 and a second end 140 thereof. The protective sleeve may be sealed with respect to first end 135 and second end 140 in a conventional manner (not shown).

Figure 2:
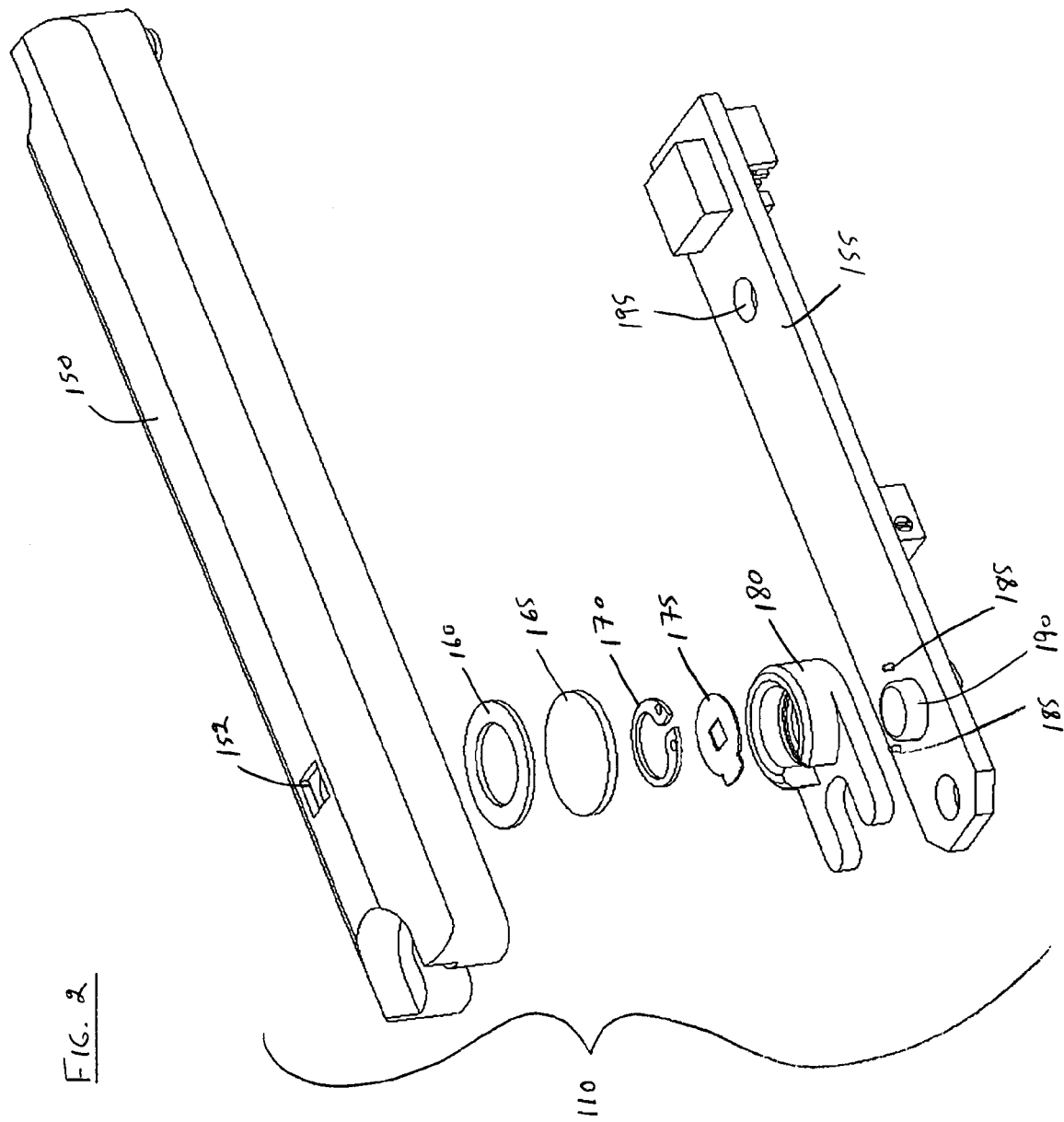
FIG. 2 illustrates a perspective view of a radiation sensor module used in FIG. 1 shown in a disassembled form viewed from an outward perspective.
Figure 3:
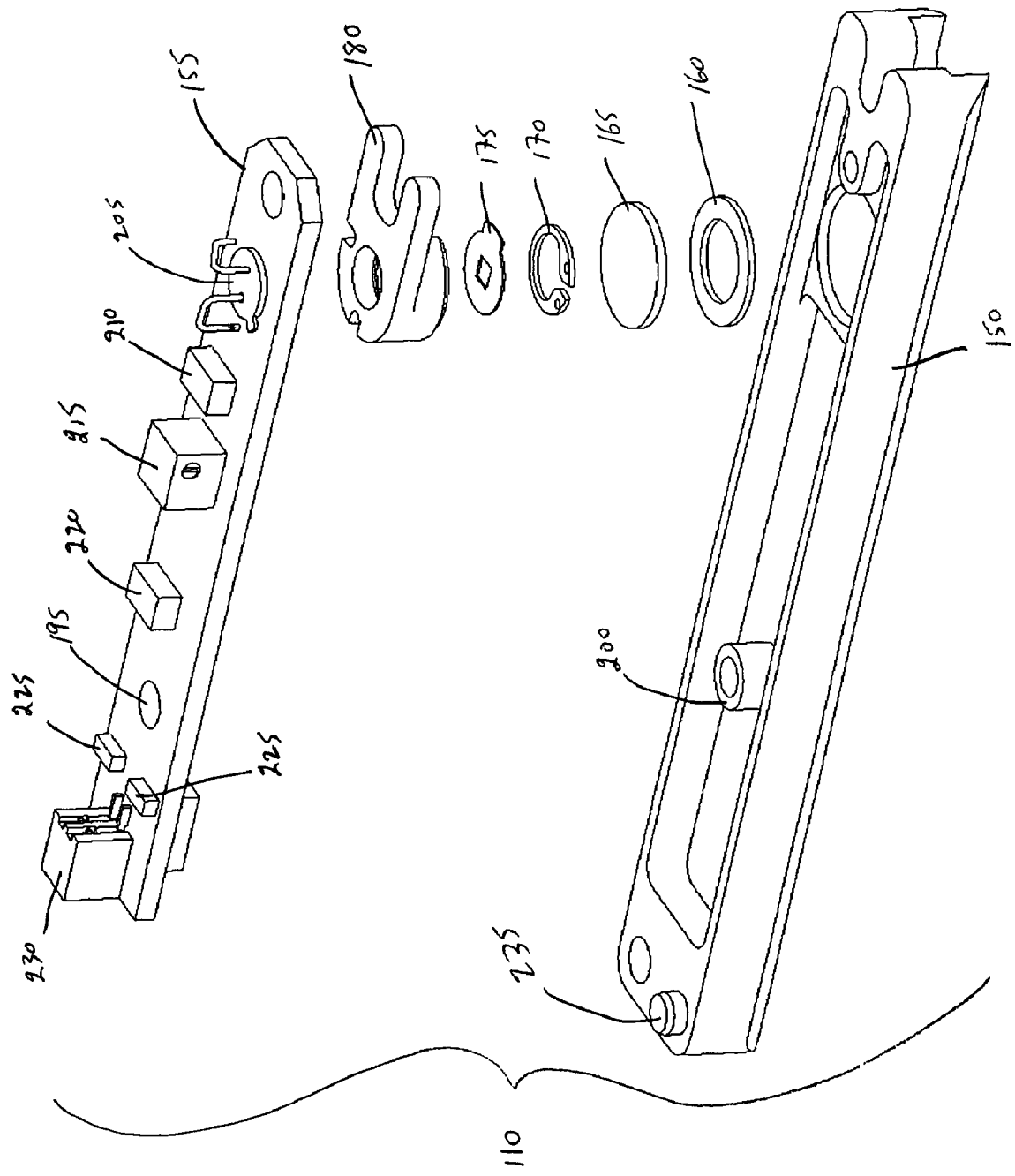
FIG. 3 illustrates a perspective view of a radiation sensor module used in FIG. 1 shown in a disassembled form viewed from an inward perspective.

With reference to FIGS. 2 and 3, there is shown an exploded view of radiation sensor module 110. As described above, the construction of radiation sensor module 110 is the same as that of radiation sensor modules 115,120.

Thus, as shown in FIG. 2, radiation sensor module 110 comprises a module housing 150 and a printed circuit board 155. Disposed in module housing 150 is a radiation transparent window (sometimes referred to in the art as an "aperture") 152 through which incident radiation may pass.

Interposed between module housing 150 and printed circuit board 155 are the following elements, in sequence: a Teflon™ washer 160, an optional radiation filter 165 (e.g., quartz, a diffraction grating and the like), a retaining ring 170, an aperture 175 and an aperture support 180. As shown, aperture support 180 is correctly located through the use of pins 185 and detector seat 190 on printed circuit board 155.

Module housing 150 and printed circuit board 155 can be secured to one another in a conventional manner—e.g., through the use of mechanical means such as screws, rivets and the like. Printed circuit board 155 further comprises a locating hole 195 which receives locator 200 on module housing 150 (FIG. 3).

Printed circuit board 155 comprises a complete so-called optical train to allow sensor module 110 to function as a sensor device. Thus, the following components are disposed on printed circuit board 155 in suitable electrical connection: a detector 205 (e.g., a photodiodes, a photoresistor and the like), a signal amplifier 210, a gain adjustment potentiometer 215 (this is equivalent to a single calibration element), a current loop transmitter 220, a pair of reverse polarity protection diodes 225 and a Molex™ connector 230.

Of course, it is possible to dispose additional components on printed circuit board 155 depending on the desired functionality of the sensor device. The important feature is that on a given radiation sensor module 110, it is possible to pair a given filter 165 with a given detector 205 and calibrate the latter through adjustment of potentiometer 215 without the need to disassemble the entire radiation sensor module. To the knowledge of the present inventors, a device having these features is heretofore unknown.

Module housing 150 comprises a locating pin 235 for engagement with a complementary shaped hole (not shown) in housing 105 of radiation sensor device 100. The use of such a locating pin/hole combination allows for correct placement of each radiation sensor module in radiation sensor device 100.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. An ultraviolet radiation sensor device comprising:
 a device housing having (i) a first longitudinal axis and (ii) at least two ultraviolet radiation sensor modules annularly disposed on the housing so as to face outward in different directions from said first longitudinal axis, each radiation sensor module comprising:

a radiation sensor arranged to detect an ultraviolet radiation incident on the radiation sensor, and a module housing having an ultraviolet radiation transparent window through which the incident ultraviolet radiation passes to contact the radiation sensor, the radiation transparent window oriented exteriorly with respect to the device housing, the radiation sensor being oriented interior of the transparent window with respect to the device housing, a radiation filter coupled to said module housing and disposed exteriorly of said radiation sensor, and a calibration element configured to calibrate said radiation sensor for the particular filter disposed exteriorly thereof.

2. The radiation sensor device defined in claim 1, wherein each radiation sensor module comprises a second longitudinal axis.

3. The radiation sensor device defined in claim 2, wherein the plurality of radiation sensors modules are secured to the device housing such that the first longitudinal axis and the second longitudinal axes are substantially parallel.

4. The radiation sensor device defined in claim 2, wherein an adjacent pair of radiation sensor modules are offset with respect to one another in a direction substantially parallel to the first longitudinal axis.

5. The radiation sensor device defined in claim 1, wherein each module housing comprises one or more of the following components: a signal amplification element, a signal calibration element, and signal transmitter element.

6. The radiation sensor device defined in claim 1, wherein each module housing comprises each of the following components: a signal amplification element, a signal calibration element, and signal transmitter element.

7. The radiation sensor device defined in claim 1, further comprising a protective sleeve substantially encompassing the plurality of radiation sensor modules, the protective sleeve comprising a radiation transparent first region and a radiation opaque second region, the radiation transparent first region being oriented to include the radiation sensor of each radiation sensor module.

8. The radiation sensor device defined in claim 7, wherein the radiation opaque second region is configured to define a plurality of radiation transparent first regions.

9. The radiation sensor device defined in claim 8, wherein the radiation opaque second region comprises a metallic layer.

10. The radiation sensor device defined in claim 9, wherein the metallic layer comprises at least one member selected from the group comprising stainless steel, titanium, aluminum, gold, silver, nickel, platinum, nitinol, and mixtures thereof.

11. The radiation sensor device defined in claim 1, wherein each radiation sensor module comprises a first locator element, and wherein the module housing comprises a second locator element, the first locator element and the second locator element being of substantially complementary shape and cooperating to secure the radiation sensor with respect to the housing.

12. The radiation sensor defined in claim 11, wherein the first locator element comprises a male portion and the second locator element comprises a female portion.

13. The radiation sensor defined in claim 11, wherein the first locator element comprises a female portion and the second locator element comprises a male portion.

14. A fluid treatment system comprising a fluid treatment zone having disposed therein a plurality of radiation sources and the radiation sensor device defined in claim 1.

15. The fluid treatment system defined in claim 14, wherein the ratio of radiation sources to radiation sensor modules is 1:1.

16. The fluid treatment system defined in claim 14, wherein the plurality of radiation sources is arranged annularly with respect to the radiation sensor device.

17. The radiation sensor device defined in claim 1, wherein each radiation sensor module comprises a single radiation sensor.

18. Ultraviolet radiation sensor apparatus submersed within a fluid flow, said apparatus comprising:

a housing having a longitudinal axis and an outer surface disposed within said fluid flow;

a plurality of ultraviolet radiation sensor modules annularly disposed on an outer surface of the housing and within the fluid flow so as to face outward in different directions from said longitudinal axis;

each ultraviolet radiation sensor module having (i) a radiation sensor and (ii) an ultraviolet radiation transparent window through which incident ultraviolet radiation passes to contact the radiation sensor, the radiation transparent window being disposed on the outer surface of the housing and within the fluid flow;

each ultraviolet radiation sensor module also having a radiation filter disposed exteriorly of said radiation sensor, and each ultraviolet radiation sensor module further having a calibration element configured to calibrate said radiation sensor for the particular filter disposed exteriorly thereof.

19. Apparatus defined in claim 18, wherein each ultraviolet radiation sensor module further comprises one or more of the following components: a signal amplification element and a signal transmitter element.

20. Apparatus defined in claim 18, wherein each ultraviolet radiation sensor module further comprises each of the following components: a signal amplification element and signal transmitter element.

21. Apparatus defined in claim 18, wherein each radiation sensor module comprises a first locator element for engagement to a second locator element located in a housing for the radiation sensor module, the first locator element and the second locator element being of substantially complementary shape and cooperating to secure the radiation sensor with respect to the housing.

22. Apparatus defined in claim 21, wherein the first locator element comprises a male portion and the second locator element comprises a female portion.

23. Apparatus defined in claim 21, wherein the first locator element comprises a female portion and the second locator element comprises a male portion.

24. Apparatus defined in claim 18, wherein each ultraviolet radiation sensor module further comprises comprising a printed circuit board to which each of the radiation sensor and the calibration element is in electrical connection.

25. Apparatus defined in claim 18, wherein the calibration element comprises a gain adjustment potentiometer.

* * * * *